US006380257B1

(12) United States Patent
Vértesy et al.

(10) Patent No.: US 6,380,257 B1
(45) Date of Patent: Apr. 30, 2002

(54) AROMATIC DI-KETO DERIVATIVES, PROCESSES FOR THEIR PRODUCTION AND THEIR USE AS A PHARMACEUTICAL

(75) Inventors: László Vértesy, Eppstein; Michael Kurz, Hofheim; Erich Paulus, Eppstein, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/694,790

(22) Filed: Oct. 24, 2000

(30) Foreign Application Priority Data

Oct. 25, 1999 (EP) .............................................. 99121241

(51) Int. Cl.$^7$ ........................ A61K 31/19; A61K 31/21; C07C 59/76; C07C 69/76; C07D 307/77
(52) U.S. Cl. ........................ 514/569; 514/568; 514/510; 514/462; 514/473; 562/461; 562/459; 560/53; 549/298; 549/449; 549/499
(58) Field of Search ............................. 560/53; 514/510, 514/569, 568, 462, 473; 522/461, 459; 549/298, 449, 499

(56) References Cited

U.S. PATENT DOCUMENTS 6,297,043 B1 * 10/2001 Ramakrishna et al. ... 435/253.5

FOREIGN PATENT DOCUMENTS

| EP | 0 587 087 A1 | 3/1994 |
| EP | 0 587 088 B1 | 3/1994 |
| EP | 0 902 002 A1 | 3/1999 |
| WO | WO 98/02247 | 1/1998 |
| WO | WO 98/47888 | 10/1998 |

OTHER PUBLICATIONS

International Search Report, dated May 5, 2000.
Hemmerle, Horst, et al., "Chlorogenic Acid and Synthetic Chlorogenic Acid Derivatives: Novel Inhibitors of Hepatic Glucose–6–phosphate Translocase," *Journal of Medicinal Chemistry*, vol. 40, No. 2, pp. 137–145 (1997).

Soodsma, James F., et al., "The Inhibition by Phlorizin of Kidney Microsomal Inorganic Pyrophosphate–Glucose Phosphotransferase and Glucose 6–Phosphatase," *The Journal of Biological Chemistry*, vol. 242, No. 8, pp. 1955–1960 (1967).

Wallin, Bruce K., and Arion, William J., "The Requirement for Membrane Integrity in the Inhibition of Hepatic Glucose 6–Phosphatase by Sulfhydryl Reagents and Taurocholate," *Biochemical and Biophysical Research Communications*, vol. 48, No. 3, pp. 694–699 (1972).

Zoccoli, Michael A., and Karnovsky, Manfred L, "Effect of Two Inhibitors of Anion Transport on the Hydrolysis of Glucose 6–Phosphate by Rat Liver Microsomes," *The Journal of Biological Chemistry*, vol. 255, No. 3, Issue of Feb. 10, pp. 1113–1119 (1980).

* cited by examiner

*Primary Examiner*—Deborah C. Lambkin
(74) *Attorney, Agent, or Firm*—Finnegan, Henderson, Farabow, Garrett & Dunner, LLP

(57) ABSTRACT

The present invention relates to new aromatic di-keto derivatives and to their pharmaceutically acceptable salts, esters, ethers and other chemical equivalents. The derivatives are glucose-6-phosphate translocase inhibitors and can be used in the treatment of diabetes mellitus. The present invention further relates to a process for the production of the derivatives, to the use of the derivatives and their pharmaceutically acceptable salts, esters, ethers and other chemical equivalents as pharmaceuticals, in particular to their use in the treatment of diabetes mellitus, and to pharmaceutical compositions comprising the derivatives, pharmaceutically acceptable salts, esters, ethers or other chemical equivalents thereof.

36 Claims, No Drawings

AROMATIC DI-KETO DERIVATIVES, PROCESSES FOR THEIR PRODUCTION AND THEIR USE AS A PHARMACEUTICAL

The present invention relates to new aromatic di-keto derivatives, and to their pharmaceutically acceptable salts, esters, ethers, and other chemical equivalents. The di-keto derivatives are glucose-6-phosphate translocase inhibitors, and can be used in the treatment of diabetes mellitus. The present invention further relates to a process for the production of the di-keto derivatives, to the use of the di-keto derivatives and their pharmaceutically acceptable salts, esters, ethers, and other chemical equivalents as pharmaceuticals, in particular to their use in the treatment of diabetes mellitus, and to pharmaceutical compositions comprising the di-keto derivatives, pharmaceutically acceptable salts, esters, ethers, or other chemical equivalents thereof.

Increased rate of hepatic glucose output is a general feature of diabetes mellitus. In particular, a strong correlation exists between fasting plasma glucose level in non-insulin dependent diabetes mellitus (NIDDM) and hepatic glucose output. The two pathways by which glucose is produced in the liver are gluconeogenesis and glycogenolysis. The terminal steps of both pathways are catalyzed by the microsomal glucose-6-phosphatase, a key enzyme in the homeostatic regulation of blood glucose levels. The level of this enzyme has also been known to be elevated in both experimental and pathological conditions of diabetes. Interference with this enzyme system should, therefore, result in a reduced hepatic glucose production.

Hepatic glucose-6-phosphatase is a multicomponent system comprised of at least three functional activities: a glucose-6-phosphate translocase (T1), a glucose-6-phosphate phosphohydrolase and a phosphate/pyrophosphate translocase (T2). The glucose-6-phosphate translocase facilitates transport of glucose-6-phosphate into the lumen of the endoplasmic reticulum (ER). The phosphohydrolase, with its active site situated on the lumenal surface of the ER, hydrolyzes glucose-6-phosphate and releases glucose and phosphate into the lumen. While the efflux of phosphate is facilitated by the phosphate/pyrophosphate translocase, the exact mechanism of glucose efflux is still not clear.

The high degree of substrate specificity of glucose-6-phosphate translocase makes this a potential target for pharmacological intervention in the treatment of diabetes mellitus. Thus, amongst physiologically occurring sugar phosphates, only glucose-6-phosphate is transported by the translocase. In contrast, the phosphatase is non-specific and is known to hydrolyse a variety of organic phosphate esters.

A series of non-specific inhibitors of glucose-6-phosphatase has been described in the literature, e.g. phlorrhizin (*J. Biol. Chem.* 242, 1955–1960 (1967)), 5,5'-dithiobis-2-nitrobenzoic acid (*Biochem. Biophys. Res. Commun.* 48, 694–699 (1972)), 2,2'-diisothiocyanatostilbene and 2-isothiocyanato-2'-acetoxystilbene (*J. Biol. Chem.* 255, 1113–1119 (1980)). The first therapeutically utilizable inhibitors of the glucose-6-phosphatase system are proposed in EP-A-587 087 and EP-A-587 088. Kodaistatins A, B, C, and D described in PCT/EP 98/02247 are the first glucose-6-phosphate translocase inhibitors from microbial sources.

The aromatic di-keto derivatives according to the present invention may be derived from a compound named mumbaistatin. Mumbaistatin is described in PCT/EP99/04127. It is a natural product obtainable by cultivation of the microorganism *Streptomyces litmocidini*, a sample of which was deposited on Jul. 4, 1997, with the German Collection of Microorganisms and Cell Cultures (DSMZ) under accession no. DSM 11641. The structural formula of mumbaistatin has now been determined and is given below:

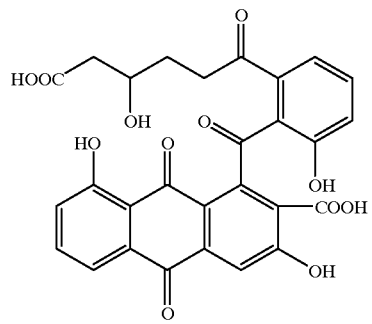

It has been found that certain derivatives of mumbaistatin have improved activity and are better tolerated in the mammalian body than mumbaistatin itself. Also, the separated diastereomers of mumbaistatin have advantages over the mumbaistatin mixture of diastereomers.

The present invention accordingly provides compounds of the general formula I

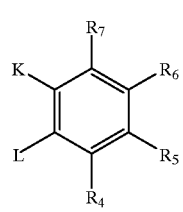

I wherein:

$R_4$, $R_5$, $R_6$ and $R_7$ are independently selected from H, OH, halogen, optionally substituted alkyl, aryl or acyl, X-alkyl, and X-aryl, where X is O, NH, N-alkyl or S, K is a group of formula II or III:

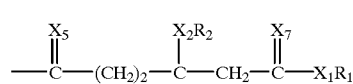

II

III

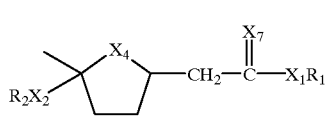

L is a group of formula IV or V:

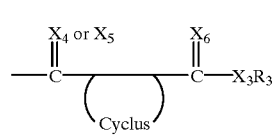

IV

-continued

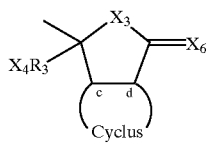

V or K and L form, together with the respective carbon atoms to which they are bound, a group of formula VI, VII, or VIII:

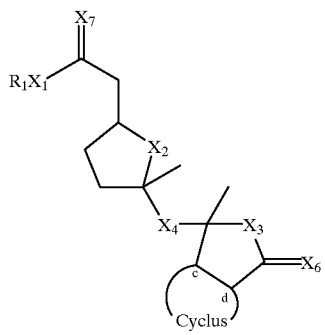

VI

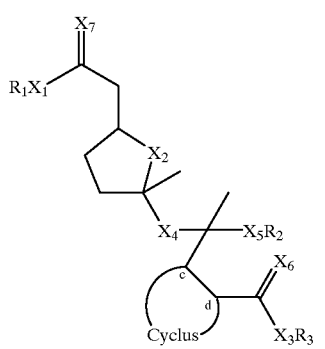

VII

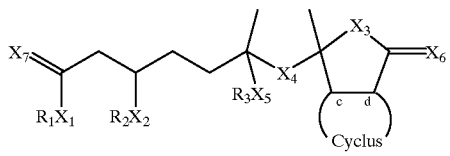

VIII wherein:
$R_1$ and $R_3$ are independently selected from a cation, H, alkyl, and aryl,
$R_2$ is H, alkyl, aryl, or acyl,
$X_1$, $X_2$, $X_3$, $X_4$, $X_5$, $X_6$ and $X_7$ are independently selected from O, NH, N-alkyl and S, and the Cyclus is, together with the C-atoms marked c' and d' an optionally substituted saturated, partly unsaturated or aromatic, carbocyclic or heterocyclic, simple or condensed ring system, and its pharmaceutically acceptable salts, esters and ethers and other chemical equivalents in all their stereoisomeric and tautomeric forms and mixtures thereof in any ratio with the exclusion of the compound where K is a group of formula II, and L is a group of formula IV in which $X_1$, $X_2$, $X_3$, $X_4$, $X_5$, X6 and $X_7$ are O, $R_1$, $R_2$ and $R_3$ are H, $R_4$ is OH, $R_5$, $R_6$ and $R_7$ are H, and Cyclus is 3,8, di-hydroxy anthraquinone, and the compound where K and L form together a group of formula VI in which $X_1$, $X_2$, $X_3$, $X_4$, $X_5$, $X_6$ and $X_7$ are O, $R_1$ is $CH_3$, $R_2$ and $R_3$ are H, $R_4$ is OH, $R_5$, $R_6$ and $R_7$ are H, and Cyclus is 3,8-dihydroxy anthraquinone.

The present invention furthermore includes compounds of the general formula IX

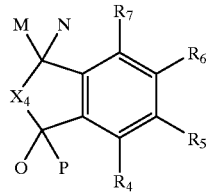

IX wherein:
M is a group of formula X

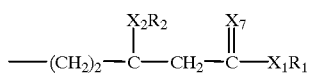

X

N is a group of formula XI $$—X_5R_3$$

XI or M and N form, together with the C atom to which they are bound, a residue of formula XII

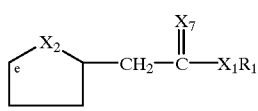

XII which is bonded through the C atom marked e
O is a group of formula XIII

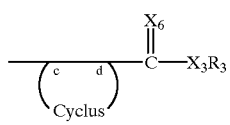

XIII and
P is a group of formula XIV $$—X_5R_2$$

XIV or O and P form, together with the C atom to which they are bound, a residue of formula XV

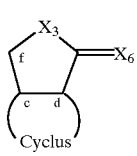

XV which is bonded through the C atom marked f
wherein $R_1$ to $R_7$, $X_1$ to $X_7$, Cyclus, c and d are as defined in claim 1, and its pharmaceutically acceptable salts, esters and ethers and other chemical equivalents in all their stereoisomeric and tautomeric forms and mixtures thereof in any ratio.

The term 'alkyl' as used herein represents a straight or branched, optionally substituted $C_1$–$C_6$-alkyl, preferably a $C_1$–$C_4$-alkyl such as: methyl, ethyl, n-propyl, i-propyl, n-butyl, or i-butyl, a straight or branched, optionally substituted, $C_2$–$C_6$-alkenyl, preferably $C_2$–$C_4$-alkenyl such as allyl, a straight or branched, optionally substituted $C_2$–$C_6$-alkynyl, preferably $C_2$–$C_4$-alkynyl such as allylene.

The term 'aryl' as used herein represents an optionally substituted benzyl or phenyl.

The term 'acyl' as used herein represents an optionally substituted aliphatic, aromatic, or heterocyclic acyl, for example $C_1$–$C_4$ aliphatic acyl, such as acetyl or propionyl, aromatic acyl, such as benzoyl or toluyl, and heterocyclic acyl which is derived from 5- or 6-membered rings with 1–4 hetero atoms, such as, nicotinoyl, furyl, pyrrolyl, thienyl, thiazolyl and oxazolyl.

'Optionally substituted' as used herein means that the group in question is optionally substituted by one or more, preferably 1, 2, 3, or 4, identical or different substituents selected from: hydroxyl, $C_1$–$C_4$alkyl, $C_1$–$C_4$alkenyl, $C_1$–$C_4$alkoxy, $C_1$–$C_4$alkylthio, $C_1$–$C_4$alkoxycarbonyl, carbamoyl, carboxyl, trifluoromethyl, cyano, nitro, amino, $C_1$–$C_4$alkylamino, di$C_1$–$C_4$alkylamino, amidino, aryloxy, arylamino and halogen.

Halogen represents I, Br, Cl, or F, preferably Cl or Br.

The term 'cation' represents an inorganic metal ion or an organic ammonium ion. Examples are pharmacologically acceptable alkali metal ions or alkaline earth metal ions, preferably sodium, potassium, calcium, or magnesium ion, the ammonium ion and, from the organic ammonium ions, in particular, an optionally substituted alkylated ammonium ion, such as, for example, the triethylammonium or diethanolammonium ion, as well as the morpholine, benzylammonium and procaine, L-arginine and L-lysine ions.

The Cyclus ring, which includes the carbon atoms marked 'c' and 'd' in the formulae, may represent an optionally substituted, saturated, partly unsaturated or aromatic, carbocyclic or heterocyclic, simple or condensed ring system. A simple ring system means a monocyclic ring containing 3 to 6 ring atoms and a condensed ring system means a condensed dicyclic or tricyclic ring containing 6 to 14 ring atoms.

The saturated carbocyclic ring system may represent a 3 to 14 membered ring system, preferably a simple 3 to 8 membered ring such as cyclo-$C_3$–$C_8$alkyl, more preferably cyclo-$C_3$–$C_6$alkyl, for example, cyclopropyl, cyclobutyl, cyclopentyl, or cyclohexyl. It may also represent a bi- or tri-cyclic condensed ring system such as bicyclo[3.3.1] nonane or tetradecahydrophenanthrene.

The partly unsaturated carbocyclic ring system differs from the saturated carbocyclic ring system in having one or two double or triple bonds. Thus, it may represent a 3 to 14 membered ring system, preferably a 3 to 8 membered ring such as cyclo-$C_3$–$C_8$alkene, for example, cyclopentadiene or cyclooctatetraene, more preferably cyclo-$C_3$–$C_6$alkene, or cyclo-$C_5$–$C_8$alkyne.

The aromatic carbocyclic simple or condensed ring system may represent a 5 to 14 membered monocyclic, dicyclic or tricyclic ring system such as phenyl, naphthyl, phenanthrene, or anthraquinone.

The heterocyclic ring system may be saturated, partly unsaturated, or aromatic and may be a simple or condensed ring system as defined above. The heterocyclic ring system represents the carbocyclic ring system as defined above in which 1, 2, 3, or 4 of the C atoms are replaced by identical or different heteroatoms selected from N, O and S. It may, for example, represent a 5- or 6-membered ring which has 1 to 4 heteroatoms, independently selected from O, S and N. in particular N, optionally together with S or O as ring atoms. Some examples of heterocyclic ring systems are heteroalkyls such as pyrrolidine, piperidine, tetrahydrofuran, oxazolidine and thiazolidine, and heteroaryl residues such as pyridyl, pyrimidyl, furanyl, benzothiazoyl, benzofuranyl and indolyl.

Preferably, the Cyclus is a group of formula XVI

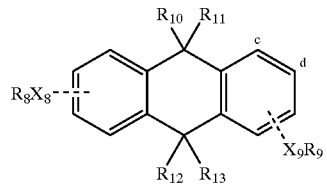

XVI wherein:

$R_8$ is H, alkyl, aryl, or acyl;

$R_9$ is a cation, H, alkyl, aryl, or acyl;

$R_{10}$, $R_{11}$, $R_{12}$ and $R_{13}$ are independently selected from H, alkyl, —$X_{10}$H, —$X_{10}$R, $R_{10}$, and $R_{11}$ and/or $R_{12}$ and $R_{13}$ together are =$X_{10}$, $X_8$, $X_9$ and $X_{10}$ are independently selected from O, NH, N-alkyl and S, R is alkyl, aryl, or acyl, ' - - - - - ' is an optional bond, and the Cyclus is bound by the C-atoms marked c and d.

More preferably the Cyclus ring is a residue of formula XVIA

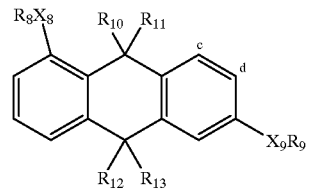

XVIA wherein:

$X_8$ and $X_9$ are independently H or O;

$R_8$ and $R_9$ are independently H or alkyl;

$R_{10}$ to $R_{13}$ are H, or $R_{10}$ and $R_{11}$ together and/or $R_{12}$ and $R_{13}$ together are a carbonyl, and the Cyclus is bound by the C-atoms marked c and d.

The Cyclus part of the structure may be any one of a variety of different ring structures. It is advantageous, however, to have a substitution, preferably hydroxyl or alkoxyl, on the Cyclus. The Cyclus is preferably an aromatic ring structure of formula XVIB below:

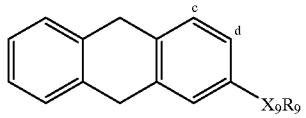

XVIB wherein;

$R_9$ is H or $C_1$–$C_4$-alkyl; and $X_9$ is O.

Preferred compounds of the present invention have the general formula XVIII:

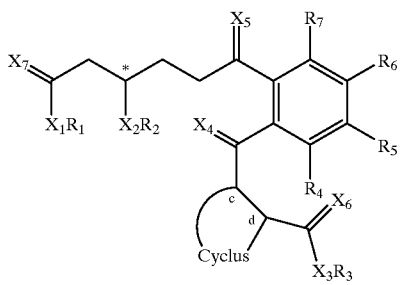

XVIII wherein:

$R_1$ to $R_7$, $X_1$ to $X_7$, Cyclus and c and d are as defined above, with the exclusion of the compound where $X_1$ to $X_7$ are O, $R_1$, $R_2$ and $R_3$ are H, $R_4$ is OH, $R_5$, $R_6$ and $R_7$ are H and Cyclus is 3,8, di-hydroxy anthraquinone, and its pharmaceutically acceptable salts, esters and ethers and other chemical equivalents, in all their stereoisomeric and tautomeric forms and mixtures thereof in any ratio.

Preferably the carbon marked with an asterisk has an S configuration, in which case the exclusion mentioned above is not applicable.

Suitably, $R_1$, $R_2$ and $R_3$ are $C_1$–$C_6$-alkyl, preferably $C_1$–$C_4$ alkyl, such as methyl.

Conveniently, any one or more of $X_1$ to $X_7$ are O.

An example of a compound of formula XVIII above is formula XVIIIA:

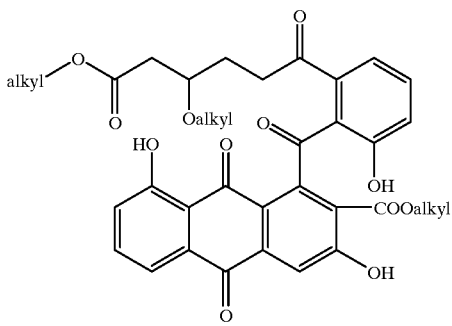

XVIIIA

A further example of a compound of formula XVIII above is formula XVIIIB:

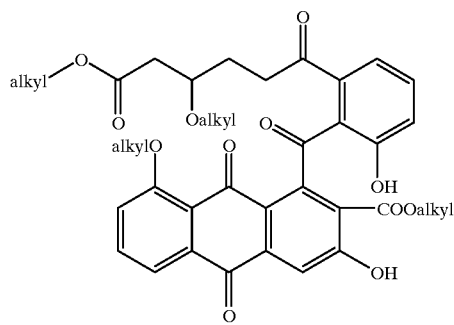

XVIIIB

The alkylated mumbaisatin derivatives of formula XVIIIA and formula XVIIIB are obtained by dissolving mumbaistatin in a solvent, preferably an organic solvent such as alkanol, for example methanol, and reacting with an alkylating agent such as diazoalkane, for example diazomethane, diazoethane, or diarylmethyldiazomethane such as diphenyldiazomethane. The alkyl substituent in the above compounds of formula XVIIIA and formula XVIIIB is preferably a $C_1$–$C_4$-alkyl. When the $C_1$–$C_4$-alkyl is methyl, for example, the methylated mumbaistatin derivatives may be obtained by reacting mumbaistain in solution with a methylating agent such as diazomethane. The mumbaistain has ideally previously been treated with acid, preferably low molecular organic acid, for example formic acid, acetic acid, or trifluoroacetic acid. The reaction product is subsequently isolated, preferably by chromatography.

Isolation of the compounds according to the present invention from the reaction medium can be effected by methods which are in themselves known and which depend on the solubility of the resulting compounds.

A further example of a compound of formula XVIII is the enantiomer of formula XVIIIC:

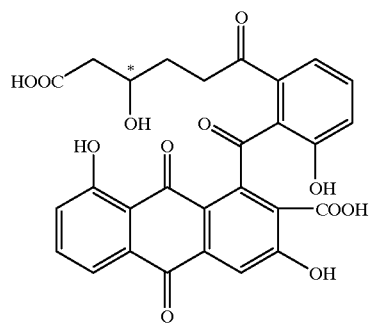

XVIIIC wherein the C atom marked with an asterisk has the S configuration.

A further example of a compound of formula XVIII according to the present invention is formula XVIIID:

XVIIID

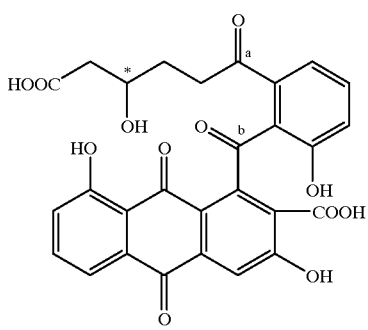

wherein the carbon atoms marked a and b in form of a half-ketal or ketal have independently the S or R configuration.

A further example of the compound of formula XVIII is formula XVIIIE:

XVIIIE

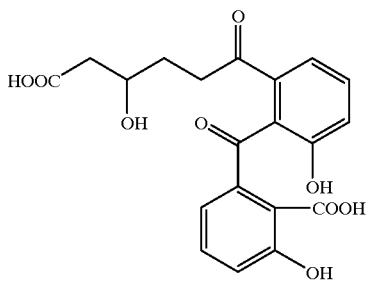

Some of the preferred compounds of formula I exemplified above may be generalized as hydroxy-diketo-dicarbonic acid derivatives.

The invention further relates to compounds of the general formula XIX:

XIX

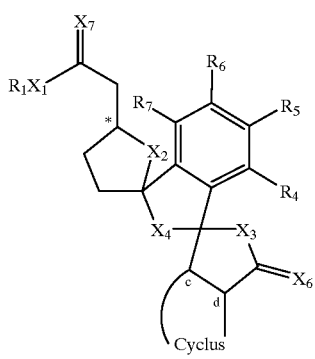

wherein $R_1$ to $R_7$, $X_1$ to $X_7$, Cyclus and c and d are as defined above, with the exception of the compound where $R_1$ is methyl, $R_4$ is —OH, $X_1$—$X_7$ are O and the Cyclus is 3,8dihydroxyanthraquinone, and its pharmaceutically acceptable salts, esters and ethers and other chemical equivalents in all their stereoisomeric and tautomeric forms and mixtures thereof in any ratio.

Preferably, $R_1$ is $C_1$–$C_6$-alkyl, such as methyl. $R_4$ is suitably hydroxy or $C_1$–$C_6$-alkoxy, such as methoxy.

An example of a compound of formula XIX is formula XIXA:

XIXA

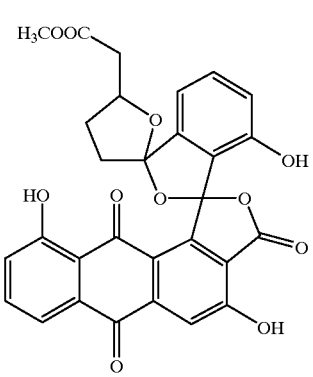

A further example of a compound of formula XIX is formula XIXB:

XIXB

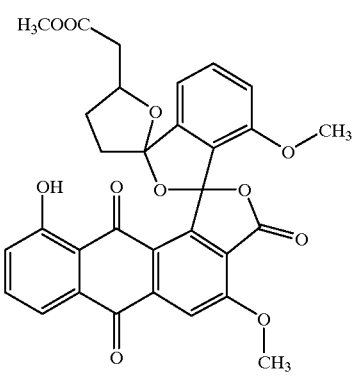

A yet further example of a compound of formula XIX is formula XIXC:

XIXC

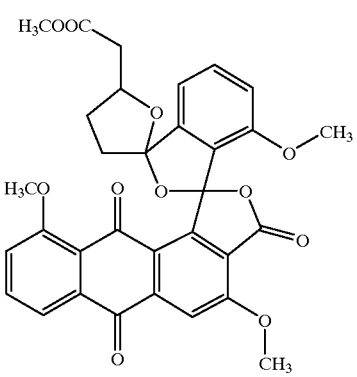

Another example of a compound of formula XIX is the diastereomer of formula XIXD:

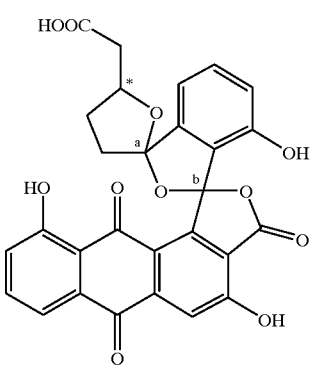

XIXD wherein the C atom marked with an asterisk * has an 'S' configuration and the C atoms marked respectively with a and b both have either an S or R configuration.

One process for the preparation of a compound of formula XIXA, XIXB, or XIXIC comprises dissolving mumbaistatin in a solvent, preferably an organic solvent, for example an alkanol such as methanol, and reacting with a methylating agent such as diazomethane. Mumbaistain has ideally previously been treated with acid such as trifluoroacetic acid. The reaction product is isolated by methods known in the art, for example, by chromatography.

Mumbaistatin is of limited stability in solution at a pH of around 6 to 9. At acid pH mumbaistatin rapidly undergoes a complex conversion, for example to the compound of formula XIXD above. Because the acid form of mumbaistain is reacted with diazomethane to produce the methylated compounds of formula XVIIIA, XVIIIB, XIXA, XIXB and XIXC above, special precautions need to be taken to ensure that native, defined methylation products are obtained It has been found that the required methylation products are obtained under cold conditions such as at temperatures of −1° C. to 3° C., preferably 0° C., and/or when the process is carried out without prolonged reaction times. It has surprisingly been possible to crystallize at least one of the methylation products by using a mixture of water and acetonitrile. This enabled determination of the structure of the compounds by X-radiation spectrometry.

TABLE 1

Crystal data and structure refinement for trimethyl-mumbaistatin (formula XVIIIA).

| | |
|---|---|
| Identification code | sh608 |
| Empirical formula | $C_{33}H_{27}NO_{11}$ |
| Formula weight | 613.56 |
| Temperature | 293(2) K |
| Wavelength | 0.71073 Å |
| Crystal system | Monoclinic |
| Space group | P2(1) |
| Unit cell dimensions | a = 12.907(4) Å  α = 90°. |
| | b = 11.253(5) Å  β = 96.56(2)°. |
| | c = 20.003(6) Å  γ = 90°. |
| Volume | 2886.2(17) Å$^3$ |
| Z | 4 |
| Density (calculated) | 1.412 Mg/m$^3$ |
| Absorption coefficient | 0.107 mm$^{-1}$ |
| F (000) | 1280 |
| Crystal size | 0.04 × 0.1 × 0.2 mm$^3$ |
| Theta range for data collection | 2.08 to 20.83°. |
| Index ranges | −12 <= h <= 12, −11 <= k <= 11, −19 <= l <= 19 |

TABLE 1-continued

Crystal data and structure refinement for trimethyl-mumbaistatin (formula XVIIIA).

| | |
|---|---|
| Reflections collected | 9796 |
| Independent reflections | 5833 [R(int) = 0.0447] |
| Completeness to theta = 20.83° | 98.7% |
| Absorption correction | maximum: 0.862, minimum: 0.632 |
| Refinement method | Full-matrix least-squares on F$^2$ |
| Data/restraints/parameters | 5833/1/822 |
| Goodness-of-fit on F$^2$ | 1.064 |
| Final R indices [l > 2 sigma (l)] | R1 = 0.0510, wR2 = 0.0966 |
| R indices (all data) | R1 = 0.0981, wR2 = 0.1171 |
| Absolute structure parameter | 1(2) |
| Extinction coefficient | 0.0035(4) |
| Largest diff. peak and hole | 0.194 and −0.174 e.Å$^{-3}$ |

TABLE 2

Chemical shifts of tetramethyl-mumbaistatin lactone di-spiroketone (Formula XIXC, CDCl$_3$, 280K).

| | A[a) $^1$H | B[a) $^1$H | A $^{13}$C | B $^{13}$C |
|---|---|---|---|---|
| 1 | — | — | 159.50 | 159.51 |
| 1-OMe | 3.87 | 3.87 | 56.28 | 56.28 |
| 2 | 7.26 | 7.26 | 118.27 | 118.27 |
| 3 | 7.67 | 7.67 | 134.57 | 134.57 |
| 4 | 7.85 | 7.85 | 119.32 | 119.32 |
| 5 | — | — | 134.44 | 134.44 |
| 6 | — | — | 183.27 | 183.24 |
| 7 | — | — | 139.57 | 139.57 |
| 8 | — | — | 124.51 | 124.50 |
| 9 | — | — | 180.29 | 180.26 |
| 10 | — | — | 122.56 | 122.50 |
| 11 | 7.88 | 7.88 | 110.55 | 110.58 |
| 12 | — | — | 160.33 | 160.33 |
| 12-OMe | 4.21 | 4.20 | 57.00 | 57.00 |
| 13 | — | — | 121.33 | 121.28 |
| 14 | — | — | 149.95 | 149.81 |
| 15 | — | — | 164.43 | 164.15 |
| 16 | — | — | 111.33 | 111.33 |
| 17 | — | — | 126.62 | 126.34 |
| 18 | — | — | 153.44 | 153.39 |
| 18-OMe | 3.54 | 3.54 | 55.52 | 55.52 |
| 19 | 6.76 | 6.77 | 110.97 | 110.92 |
| 20 | 7.46 | 7.47 | 132.15 | 132.23 |
| 21 | 7.12 | 7.09 | 114.38 | 114.32 |
| 22 | — | — | 141.76 | 142.18 |
| 23 | — | — | 119.28 | 119.58 |
| 24 | 2.74/2.58 | 2.70/2.63 | 36.05 | 35.22 |
| 25 | 2.41/1.92 | 2.41/1.97 | 30.36 | 29.87 |
| 26 | 4.77 | 4.77 | 77.64 | 76.54 |
| 27 | 2.90/2.63 | 2.86/2.63 | 41.46 | 40.15 |
| 28 | — | — | 171.74 | 171.21 |
| 28-OMe | 3.67 | 3.71 | 51.72 | 51.78 |

[a)A and B correspond to both diastereomer forms (ratio A:B approx. 1.2:1.0).

TABLE 3

Comparison of the aromatic proton chemical shifts of formula XVIIIA and formula XIXC.

| Position | Formula XVIIIA | Formula XIXC |
|---|---|---|
| 2 | 7.29 | 7.26 |
| 3 | 7.59 | 7.67 |
| 4 | 7.85/7.84 | 7.85 |
| 11 | 7.91/7.90 | 7.88 |
| 19 | 6.92 | 6.76/6.77 |
| 20 | 7.68/7.67 | 7.46/7.47 |
| 21 | 6.92 | 7.12/7.09 |

TABLE 4

Chemical shifts of Mumbaistatin lactone-di-spiroketal-monomethylester (formula XIXA), DMSO, 300K.

| Position | XIXA $^1$H | XIXA $^{13}$C |
|---|---|---|
| 1 | — | 161.38 |
| 1-OH | 13.26 | — |
| 2 | 7.18 | 123.82 |
| 3 | 7.62 | 135.15 |
| 4 | 7.57 | 117.95 |
| 5 | — | 132.68 |
| 6 | — | 183.53 |
| 7 | — | 138.70 |
| 8 | — | 117.91 |
| 9 | — | 183.09(broad) |
| 10 | — | 116.48 |
| 11 | 7.16(broad) | ~122.1(broad) |
| 12 | — | 153.87(broad) |
| 12-OH | broad | — |
| 13 | — | a) |
| 14 | — | a) |
| 15 | — | 166.45(broad) |
| 16 | — | 110.11 |
| 17 | — | 124.64, 124.51 |
| 18 | — | 151.14, 151.09 |
| 18-OH | 9.51, 9.52 | — |
| 19 | 6.68 | 115.32 |
| 20 | 7.26, 7.27 | 130.72, 130.78 |
| 21 | 6.97, 6.95 | 112.45 |
| 22 | — | 143.49, 143.68 |
| 23 | — | 117.93, 118.01 |
| 24 | 2.53/2.45, 2.59/2.37 | ~35.8(broad), ~34.9(broad) |
| 25 | 2.26/1.74, 2.22/1.85 | ~29.8(broad), ~29.4(broad) |
| 26 | 4.60, 4.54 | 76.84, 75.91 |
| 27 | 2.68, 2.63 | 41.09, 39.88 |
| 28 | — | 170.97, 170.86 |
| 28-OMe | 3.59, 3.61 | 51.22, 51.28 | a) For these nuclei, no signal was observed in the $^{13}$C-spectrum.

Where two sets of signals were observed (ratio approx. 1.1:1.0), they corresponded to the two diastereomer forms. Both values are separated by a comma in the case where the diastereomers show different chemical shifts (the first value corresponds to the main component).

The invention also relates to a compound of the general formula XX

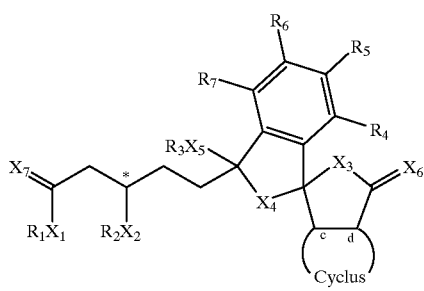

XX wherein $R_1$ to $R_7$, $X_1$ to $X_7$, Cyclus and c and d are as defined above, and its pharmaceutically acceptable salts, esters, and ethers, and other chemical equivalents, in all their stereoisomeric and tautomeric forms and mixtures thereof in any ratio. Preferably, one or more of $X_1$ to $X_7$ are O.

The invention furthermore relates to compounds of the general formula XXI:

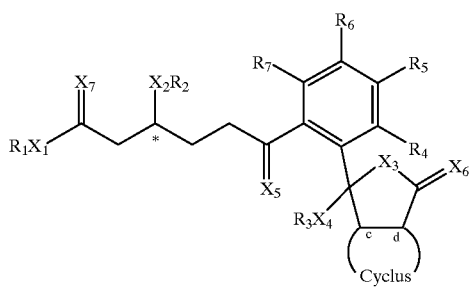

XXI wherein:
$R_1$ to $R_7$, $X_1$ to $X_7$, Cyclus and c and d are as defined above, and
its pharmaceutically acceptable salts, esters, and ethers, and other chemical equivalents, in all their stereoisomeric and tautomeric forms, and mixtures thereof in any ratio. Preferably, one or more of $X_1$ to $X_7$ are O.

The invention additionally relates to a compound of the general formula XXII

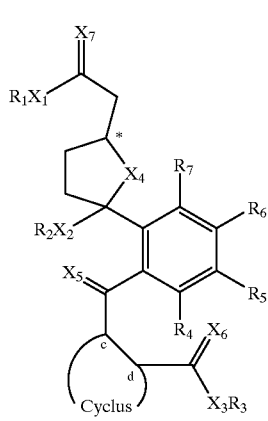

XXII wherein
$R_1$ to $R_7$, $X_1$ to $X_7$, Cyclus and c and d are as defined above, and
its pharmaceutically acceptable salts, esters, and ethers, and other chemical equivalents, in all their stereoisomeric and tautomeric forms, and mixtures thereof in any ratio. Preferably, one or more of $X_1$ to $X_7$ are O.

An example of a compound of formula XXII is given below:

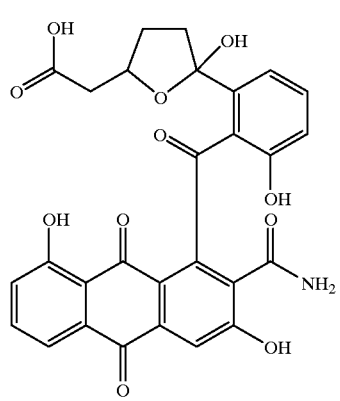

XXIIA

A process for the preparation of a compound of formula XXIIA comprises dissolving mumbaistatin in a solvent, preferably an organic solvent such as alkanol, and reacting with an amide source such as an ammonia solution. The process is carried out under cold conditions, preferably at a temperature of −1° C. to 3° C., more preferably at 0° C. The reaction product is subsequently isolated.

The invention furthermore relates to compounds of the general formula XXIV

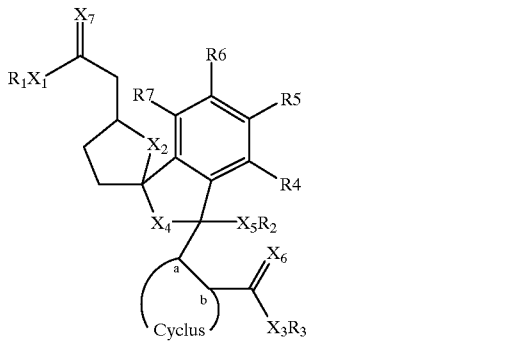

XXIV wherein:

$R_1$ to $R_7$, $X_1$ to $X_7$, Cyclus and c and d are as defined above, and its pharmaceutically acceptable salts, esters and ethers and other chemical equivalents, in all their stereoisomeric and tautomeric forms and mixtures thereof in any ratio. Preferably, one or more of $X_1$ to $X_7$ are O.

The compounds according to the present invention are tautomers in which open and closed forms exist in equilibrium.

The closed structures of formula XIX to XXIV above can be converted to the open structure of formula XVIII by reaction with a suitable base. Suitable bases which can be used for the reaction are inorganic or organic bases. Thus, tertiary amines and alkali metal carbonates, such as sodium carbonate, sodium bicarbonate, potassium bicarbonate, potassium carbonate, lithium carbonate may be used.

An example of tautomers according to the present invention in equilibrium are compounds of formula XXIIIA and XVIIIF:

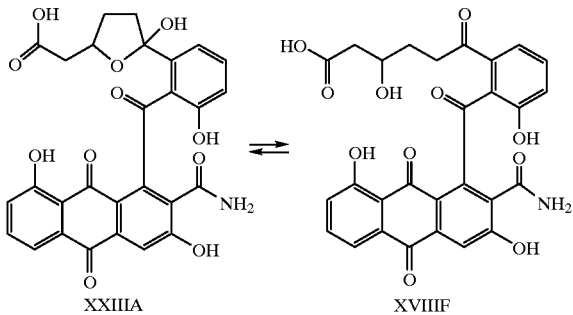

XXIIIA    XVIIIF

The compounds according to the invention may be converted into pharmaceutically acceptable salts and chemical equivalents, such as esters and ethers, which are all covered by the present invention. The invention also covers all salts and chemical equivalents of the present compounds which themselves are not suitable for use as pharmaceuticals but which can be used as intermediates in the preparation of pharmaceutically acceptable salts and derivatives. The invention covers the present aromatic di-keto derivatives and their salts, esters, ethers and other chemical equivalents in all their stereoisomeric forms and tautomeric forms. The salts of the derivatives (e.g. Na, K, ammonium salts) can be prepared by standard procedures known to one skilled in the art. Salts like sodium and potassium salts, for example, may be prepared by treating the present compounds with suitable sodium or potassium bases.

Esters may be prepared, for example, by reacting the present compounds with carboxylic acids in the presence of reagents such as dicyclohexylcarbodiimide (DCC), or by treating the compound with acylating agents such as acid chlorides. Other methods of preparation of esters are given in the literature, for example in J. March, *Advanced Organic Synthesis*, 4th Edition, John Wiley & Sons, 1992.

Ethers may be prepared, for example, from mumbaistatin by reaction with alkylating agents under basic conditions. Other methods of preparation of ethers are given in the literature, for example in *Advanced Organic Synthesis*, 4th Edition, J. March, John Wiley & Sons, 1992.

Other chemical equivalents include reduction or oxidation products and addition products such as hydrates. For example, the anthraquinone group of mumbaistatin may be reduced with a reducing agent to hydroquinone. The resultant product is an effective inhibitor of glucose-6-phosphate translocase with an $IC_{50}$ of=~5 nM.

Glucose-6-phosphate translocase activity has been shown in several biochemical test systems for mumbaistatin. The yield of mumbaistatin from the culture filtrate of *Streptomyces litmocidini* is extremely low, however, which has hindered further development of the compound. Moreover, until now it has not been possible to ascertain the structural formula of mumbaistatin due of numerous factors including the compound's inability to crystalize and its instability in solution.

A process has now been found, however, which enables the isolation of mumbaistatin from an extract in relatively high yield. The present invention accordingly provides a process for the isolation of mumbaistatin comprising extracting a culture filtrate including mumbaistatin by ion exchange chromatography at a pH of 5–8, preferably 6 or 7. Although the use of ion exchange is generally mentioned in PCT/EP99/04127, the use of ion exchange for the purpose of improving yield was not recognized. Therefore, the examples in patent application PCT/EP99/04127 did not use ion exchangers for the isolation of mumbaistatin. Additionally, in application PCT/EP99/04127, 730 liters of culture filtrate yielded merely 70 mg of pure mumbaistain. The process of the present invention allows the isolation and enrichment of mumbaistatin and mumbaistain-related compounds by means of an ion exchange process whereby yields of at least more than 50%, typically >70%, are obtained. Further, the mumbaistain obtained according to the present process has an improved $IC_{50}$ of=~5 nM in comparison to the mumbaistatin obtained in PCT/EP99/04127.

In the process for the isolation of mumbaistatin according to the present invention various ion exchangers may be used. Examples are QAE-, DEAE- and THAE-anion exchangers. Particularly, substituted or unsubstituted amino groups are carried on the chosen matrix. More particularly, DEAE-anion exchangers are used, such as DEAE-SEPHAROSE FAST FLOW® or FRACTOGEL® EMD DEAE. The anion exchangers may be used in a typical manner. An organic solvent content of 5 to 85% in a buffer system may be used. It is preferable, however, that the organic solvent used has a high content of buffer system, preferably therefore, an organic solvent content of 10 to 40% in the aqueous buffer solution is used. Examples of suitable organic solvents are water-miscible organic solvents such as lower alcohols, ketones, acetonitrile, glycol, dioxane, dimethyl sulfoxide, formamide and the like. Of particular interest are solvents such as methanol, ethanol, isopropanol, and acetone.

With the process described herein, >99% pure mumbaistatin can be obtained and the compound can be enriched with a yield of more than 70%. The resultant enriched mumbaistatin may be purified in a simple manner by, for example, molecular sieve- and/or reverse-phase-chromatography.

The compounds according to the invention inhibit rat liver microsomal glucose-6-phosphate translocase. The compounds are therefore useful as pharmaceutically active ingredients, in particular in the treatment of diabetes mellitus, and more generally in the treatment or prophylaxis of conditions which are caused by, or associated with, an elevated activity of glucose-6-phosphate translocase, or of conditions in which it is intended to reduce glucose-6-phosphate translocase activity. The compounds according to the present invention and their pharmaceutically acceptable salts, esters, ethers, and other chemical equivalents can be administered to animals, particularly to mammals, and most particularly to humans, as pharmaceuticals on their own, in mixtures with one another and in the form of pharmaceutical compositions which permit enteral or parenteral administration. Accordingly, the present invention also relates to aromatic di-keto derivatives and their pharmaceutically acceptable salts, esters, ethers, and other chemical equivalents for use as pharmaceuticals and to the use of the derivatives and their pharmaceutically acceptable salts, esters, ethers and other chemical equivalents for the production of medicaments for reducing glucose-6-phosphate translocase activity, in particular for the production of medicaments for the treatment of diabetes mellitus. The present invention further relates to pharmaceutical compositions which contain an effective amount of the di-keto derivatives and/or one or more pharmaceutically acceptable salts, esters, ethers, and/or chemical equivalents thereof together with a pharmaceutically acceptable carrier.

The compounds according to the invention can be administered orally, intramuscularly, intravenously, or by other modes of administration. Pharmaceutical compositions which contain the present compounds or a pharmaceutically acceptable salt or chemical equivalent thereof, singly or in combinations, can be prepared according to standard techniques by mixing the compound(s) with one or more pharmacologically acceptable excipients and/or auxiliaries such as fillers, emulsifiers, lubricants, masking flavours, colorants, or buffer substances, and converting the mixture into a suitable pharmaceutical form such as tablets, coated tablets, capsules, or a suspension or solution suitable for enteral or parenteral administration.

Examples of auxiliaries and/or excipients are starch, tragacanth, lactose, talc, agar-agar, polyglycols, ethanol, and water. Suitable and preferred for parenteral administration are suspensions or solutions in water. It is also possible to administer the active substances directly, without vehicles or diluents, in a suitable form, for example, in capsules. Pharmaceutical compositions comprising one or more of the present compounds or a pharmaceutically acceptable salt or chemical equivalent may also contain other pharmaceutically active ingredients. As customary, the galenic formulation and the method of administration as well as the dosage range which are suitable in a specific case depend on the species to be treated and on the state of the respective condition or disease, and can be optimized using methods known in the art. On an average, the daily dose of a compound according to the present invention in a patient of about 75 mg weight is at least 0.001 mg to at most 100 mg, preferably at most 10.0 mg.

Apart from use as pharmaceutically active ingredients and as intermediates in the production of derivatives, the present compounds and their salts and chemical equivalents can also be employed as auxiliaries for diagnostic purposes, for example in in vitro diagnoses, and for research purposes in biochemical investigations in which an inhibition of glucose-6-phosphate translocase is desired.

The following examples are illustrative of the present invention, but not limitative of the scope thereof.

Abbreviations: MeOH methanol; DMSO dimethylsulfoxide; TFA trifluoroacetic acid

EXAMPLE 1

Maintenance of the culture *Streptomyces litmocidini*, DSM 11641.

Culture DSM 11641 was maintained on the following medium:

Malt extract: 10.0 g

Yeast extract: 4.0 g

Glucose: 4.0 g

Agar powder: 13.0 g

Demineralized water: 1.0 liter pH: 7.0

After dissolving the above mentioned ingredients thoroughly by heating, it was distributed in test tubes and then sterilized at 121° C. for 20 minutes. The test tubes were then cooled and allowed to solidify in a slanting position. The agar slants were streaked with the growth of the culture *Streptomyces litmocidini*, DSM 11641, by a wire loop and incubated at 28° C. (±1° C.) until a good growth was observed. The well grown cultures were stored in the refrigerator at 8° C.

EXAMPLE 2

Fermentation of culture *Streptomyces litmocidini*, DSM 11641, in fermenters.

Stage 1: Preparation of Seed Culture in Shake Flasks

Composition of seed medium:

Glucose: 15.0 g

Soyabean meal: 15.0 g

Corn steep liquor: 5.0 g

NaCl: 5.0 g $CaCO_3$: 2.09 g

Demineralized water: 1.0 liter pH: 7.0

The above seed medium was distributed in 160 ml amounts in 1 L Erlenmeyer flasks and autoclaved at 121° C. for 20 minutes. The flasks were cooled to room temperature and each flask was then inoculated with a loopful of the above mentioned well grown culture of Example 1 and shaken on a rotary shaker for 72 hours at 240 rpm at 27° C. (±1° C.) to give seed culture.

Composition of the production medium

Glucose: 20.0 g

Soyabean meal: 10.0 g $CaCO_3$: 0.2 g

Cobalt chloride: 0.001 g

Demineralized water: 1.0 liter pH: 7.0

Stage 2: Preparation of Seed Culture in Fermenter 80 liters of the seed medium, as described above, in a 100 liter Marubishi fermenter was sterilized in situ for 45 minutes at 121° C., cooled to 27° C.±1° C. and seeded with 4.5 liters of the seed culture mentioned above.

The fermentation was run with the following parameters:

Temperature: 27° C. (±0.5° C.)

Agitation: 80 rpm

Aeration: 50 lpm

Harvest time: 24 hours

Stage 3: Large Scale Fermentation 700 liters of the production medium, as described above, in a 1000 liter Marubishi fermenter along with 150 ml of DESMOPHEN® (polypropylene oxide) as antifoam agent was sterilized in situ for 45 minutes at 121° C., cooled to 27° C.±1° C. and seeded with 75 liters of the seed culture from Stage 2.

The fermentation was run with the following parameters:

Temperature: 27° C. (±0.5° C.)

Agitation: 50 rpm

Aeration: 450 lpm

Harvest time: 40–44 hours

The production of the compound was monitored by measuring the inhibition of glucose-6-phosphate translocase. When fermentation was discontinued, the pH of the culture broth was 6.0–7.0. The culture broth was centrifuged after harvesting and the glucose-6-phosphate translocase inhibitor Mumbaistatin was isolated from the culture filtrate as described below in Example 3.

EXAMPLE 3

Isolation of Mumbaistatin by Anion Exchange

Approximately 200 liters of culture broth was harvested and separated from mycelium (12 kg) by centrifugation. The desired compound Mumbaistatin was found to be present primarily in the culture filtrate. The culture filtrate (180 liters with 120 mg mumbaistatin) was passed over a column filled with adsorption resin MCI GEL CHP20P® (20 cm diameter×45 cm height, content 14 liters). The column was eluted with a gradient process of from 120 liters 0.1% phosphate buffer, pH 6.3 to 120 liters 45% isopropanol in water. The column through-flow was 18 liters/hour. The largest amount of mumbaistatin (102 mg in 12 liters) was present in the salt-free fraction which was eluted with a step gradient of 25 to 28% isopropanol in water. The resultant active eluate was passed through DEAE-SEPHAROSE FAST FLOW® filled column (3 liters) which had been equilibrated to pH 7.0 with phosphate buffer. Mumbaistatin was eluted in a gradient process with 20% isopropanol in 0.1% sodium phosphate buffer, pH 7.0 as A-buffer and 20% isopropanol in 0.1% phosphate buffer and 0.25% NaCl as B-buffer. Using a flow rate of 50 ml /min., 100 fractions were collected in which fractions 72 to 74 contained 81 mg of highly enriched mumbaistatin and fraction 75 a further 18 mg which was less pure. The fractions were pooled and concentrated under vacuum. The material was further purified by passing through a NUCLEOSIL® 100-10 $C_{18}AB$ column (2.1 cm×25 cm) and eluted at pH 6.3 with a step gradient of 5–35 % acetonitrile in 0.05% ammonium acetate buffer. Freeze drying of the pure fractions resulted in a total of 86 mg (73+13 mg) pure mumbaistatin ammonium salt.

The sodium salt of mumbaistatin was prepared by dissolving 40 mg of the ammonium salt in 10 ml water (pH 6.4) and increasing the flow of the solution with sodium chloride to 12 $mS/cm^2$. The resultant aqueous solution was then passed over a MCI GEL CHP20P® column (1 cm wide×9 cm high). The elution results with a water/40% acetonitrile in water gradient, the column flow was 5 ml per minute and the fraction sizes were 10 ml. In fractions 16 to 19 the sodium salt was found and the purifed solution had a pH of 8.5. From these fractions resulted 32 mg mumbaistatin sodium salt after freeze-drying with a purity of 99%, measured by HPLC.

UV maxima, dissolved in methanol:

219 nm, $\epsilon=33000$;

257 nm, $\epsilon=19500$;

285 nm, $\epsilon=19000$;

414 nm, $\epsilon=5100$.

Inhibition of glucose-6-phosphate translocase from rat liver microsomes was with an $IC_{50}$ of=5 nM. Inhibition of microsomal glucose-6-phosphatase in 10 $\mu$M solution: activity was not demonstrable.

EXAMPLE 4

Mumbaistatin Methylation Products 18 mg mumbaistatin obtained according to Example 3 was dissolved in 50 ml water, cooled to 0° C. and maintained at a pH of 2.8 with cold trifluoroacetic acid (TFA). Directly thereafter the resultant mixture was passed over a column (1 cm×8 cm) filled with 6.2 ml MCI GEL®, CHP20P, (75–150 um), and eluted using a gradient of 0.01% TFA to 30% acetonitrile in 0.01% TFA. The flow rate was 2.5 ml/min. The eluates were cooled and the mumbaistatin-containing fractions directly frozen to −40° C. and lyophilized.

The freeze-dried product (15 mg) was dissolved in methanol and methylated with diazomethane. After concentration in vacuum the reaction mixture, a mixture of more than ten methylation products was separated by passing over LICHROSORB® RP18, 10 u, column with dimensions 1 cm×25 cm (width×length). Acetonitrile in water, 5 to 55%, was used as the solution. The fractions were pooled cold and maintained under cold conditions during further processing. The fractions were concentrated under vacuum. Fraction 19 was mumbaistatin-mono-methylether-dimethyl ester corresponding to formula XVIIIA having a molecular weight of 590. The characteristic NMR data for the compound are shown in Table 3. Inhibition of glucose-6-translocase by a 3 $\mu$M solution: 42%.

A compound corresponding to formula XIXB was obtained from fraction 34 after concentration in vacuum under cold conditions. Crystallographic data for the compound are presented in Table 1. There exist the diastereomers S,R,R and S,S,S for the compound which are shown above. Inhibition of glucose-6-phosphate translocase: $IC_{50}=$ >100 $\mu$M.

Fraction 26 contained a compound which, after storage, was the mumbaistatin tetramethyl derivative corresponding to formula XIXC. The relevant $^1H$ and $^{13}C$-NMR data for this compound are presented in Table 2.

EXAMPLE 5

Mumbaistatin Hemiketal-amide (Formula XXIIIA)

A 1 ml concentrated aqueous ammonia solution was added dropwise under an argon atmosphere at 0° C. with stirring to a solution of 10 ml mumbaistatin in 1 ml methanol. The mixture was stirred at this temperature for 2 hours and subsequently the solution was removed in vacuum. 10 mg mumbaistatin-amide was obtained in the form of a beige powder. The molecular weight (548, M+H$^+$) was determined by electron spray mass spectrometry corresponding to the chemical formula $C_{28}H_{21}NO_{11}$.

1H-NMR (500 MHz, DMSO-d6): δ=7.8 (d, 1H), 7.75 (t, 1H), 7.35 (m, 1H), 7.25 (s, 1H), 6.85 (t, 1H), 6.55 (d, 1H), 3.85 (m, 1H), 2.2–2.35 (m), 2.05 (m, 1H), 1.8 (m, 1H), 1.2–1.4 (m) ppm.

Mumbaistatin amide of formula XXIIIA inhibites glucose-6-phosphate translocase with an $IC_{50}$=~1 μm

EXAMPLE 6
Manufacture of Mumbaistatin Lactone Diketal Monomethyl-esters 10 mg mumbaistatin obtained from Example 3 was dissolved in 1 ml absolute methanol, reacted with 0.1% strength aqueous TFA and allowed to stand at room temperature for 5 hours. The reaction product was purified by preparative chromatography as described in Example 3 and after freeze-drying the active fractions contained 7 mg of mumbaistain lactone mono methyl ester (formula XIXA). The molecular weight of the compound was 544 Da (ESI-MS).

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A compound of formula I

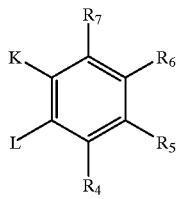

I wherein:

$R_4$, $R_5$, $R_6$ and $R_7$ are independently selected from H, OH, halogen, alkyl, aryl, acyl, X-alkyl, and X-aryl, wherein X is O, NH, N-alkyl, or S, and wherein alkyl, acyl, and aryl are optionally substituted; K is a group of formula II or III:

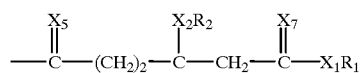

II

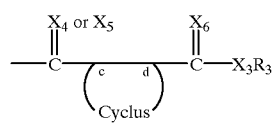

III

L is a group of formula IV or V:

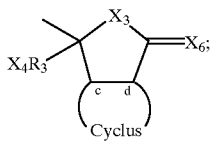

IV

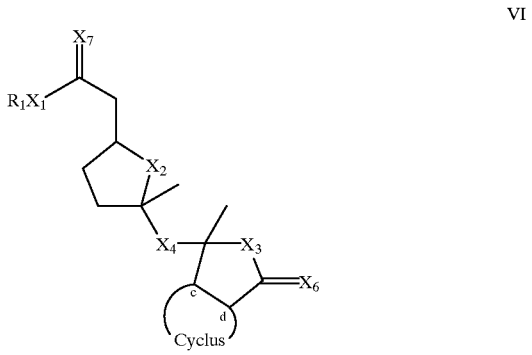

V or K and L form, together with the respective carbon atoms to which they are bound, a group of formula VI, VII, or VIII:

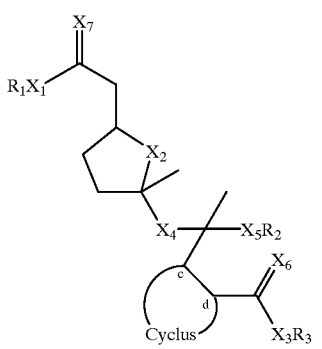

VI

VII

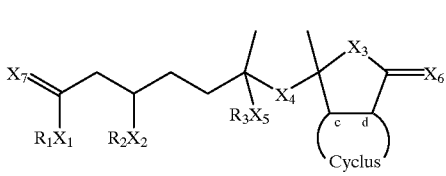

VIII wherein:

$R_1$ and $R_3$ are independently selected from a cation, H, alkyl, and aryl;

$R_2$ is H, alkyl, aryl, or acyl;

$X_1$, $X_2$, $X_3$, $X_4$, $X_5$, $X_6$, and $X_7$ are independently selected from O, NH, N-alkyl, and S, and Cyclus is, together with the C atoms marked c and d, an optionally substituted saturated, partly unsaturated, or aromatic, carbocyclic or heterocyclic, simple or condensed ring system, or a pharmaceutically acceptable salt, ester, or ether, or other chemical equivalent, in any stereoisomeric or tautomeric form, or a mixture thereof in any ratio;

with the exclusion of compounds wherein K is a group of formula II, and L is a group of formula IV in which $X_1$, $X_2$, $X_3$, $X_4$, $X_5$, $X_6$ and $X_7$ are O, $R_1$, $R_2$ and $R_3$ are H, $R_4$ is OH, $R_5$, $R_6$ and $R_7$ are H and Cyclus is 3,8-dihydroxyanthraquinone, and with the exclusion of compounds wherein K and L form together a group of formula VI in which $X_1$, $X_2$, $X_3$, $X_4$, $X_5$, $X_6$ and $X_7$ are O, $R_1$ is —$CH_3$, $R_2$ and $R_3$ are H, $R_4$ is OH, $R_5$, $R_6$ and $R_7$ are H, and Cyclus is 3,8-dihydroxyanthraquinone.

2. A compound as claimed in claim I of formula IX

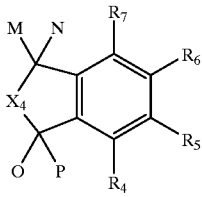

IX wherein:

M is a group of formula X

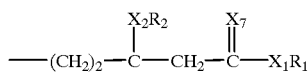

X

N is a group of formula XI

XI, or M and N form, together with the C atom to which they are bound, a residue of formula XII

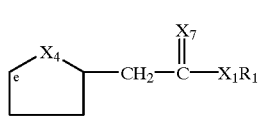

XII which is bonded through the C atom marked e;

O is a group of formula XIII

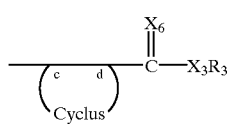

XIII

P is a group of formula XIV

XIV, or O and P form, together with the carbon atom to which they are bound, a residue of formula XV:

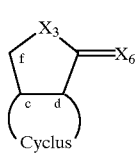

XV which is bonded through the C atom marked f;
and wherein $R_1$ to $R_7$, $X_1$ to $X_7$, Cyclus, c and d are as defined in claim 1, or a pharmaceutically acceptable salt, ester, or ether, or other chemical equivalent, in any stereoisomeric or tautomeric form, or a mixture thereof in any ratio.

3. A compound as claimed in claim 1 of formula XVIII

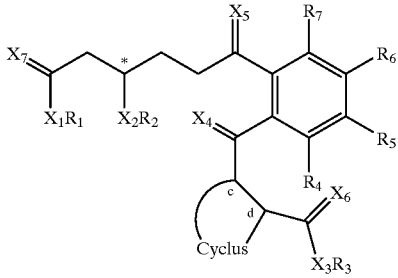

XVIII wherein $R_1$ to $R_7$, $X_1$ to $X_7$, Cyclus, c and d are as defined in claim 1,
or a pharmaceutically acceptable salt, ester, or ether, or other chemical equivalent, in any stereoisomeric or tautomeric form, or a mixture thereof in any ratio.

4. A compound as claimed in claim 3, wherein $R_1$, $R_2$, and $R_3$ are alkyl.

5. A process for preparing a compound of formula XVIII as claimed in claim 4, comprising reacting a compound of formula XVIII wherein at least one of $R_1$, $R_2$ and $R_3$ is H with an alkylating agent, and isolating a compound of the formula XVIII as claimed in claim 4.

6. A compound as claimed in claim 1 of formula XIX

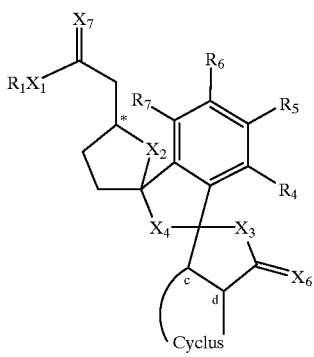

XIX wherein:

$R_1$, $R_4$ to $R_7$, $X_1$ to $X_7$, CyClus, C and d are as defined in claim 1, or a pharmaceutically acceptable salt, ester, or ether, or other chemical equivalent, in any stereoisomeric or tautomeric form, or a mixture thereof in any ratio.

7. A compound as claimed in claim 6, wherein $R_1$ is alkyl, and $R_4$ is OH or alkoxy.

8. A process for preparing a compound as claimed in claim 6, comprising reacting a solution of the compound of formula XIX wherein $R_1$ is H, and $R_4$ is OH, with an alkylating agent, and isolating a compound of formula XIX as claimed in claim 6.

9. A process for preparing a compound as claimed in claim 7, comprising reacting a solution of the compound of formula XIX wherein $R_1$ is H, and $R_4$ is OH, in an alkyl alcohol with an acid, and isolating a compound of formula XIX as claimed in claim 7.

10. A compound of formula XX as claimed in claim 1

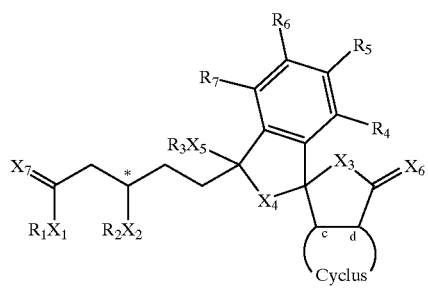

XX wherein:
$R_1$ to $R_7$, $X_1$ to $X_7$, Cyclus, c and d are as defined in claim 1,
or a pharmaceutically acceptable salt, ester, or ether, or other chemical equivalent, in any stereoisomeric or tautomeric form, or a mixture thereof in any ratio.

11. A compound of formula XXI as claimed in claim 1

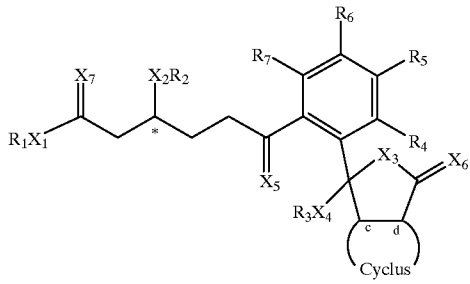

XXI wherein:
$R_1$ to $R_7$, $X_1$ to $X_7$, Cyclus, c and d are as defined in claim 1, or
a pharmaceutically acceptable salt, ester, or ether, or other chemical equivalent, in any stereoisomeric or tautomeric form or a mixture thereof in any ratio.

12. A compound as claimed in claim 1 of formula XXII

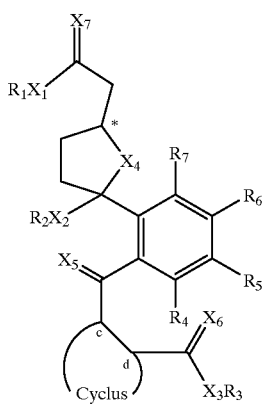

XXII wherein:
$X_1$ to $X_7$, $R_1$ to $R_7$, Cyclus, c and d are as defined in claim 1, or
a pharmaceutically acceptable salt, ester, or ether, or other chemical equivalent, in any stereoisomeric and tautomeric form or a mixture thereof in any ratio.

13. A compound of formula XXII as claimed in claim 12, wherein $R_1$ to $R_7$ are H, $X_3$ is NH, and $R_4$ is OH.

14. A compound as defined in claim 1 of formula XXIV

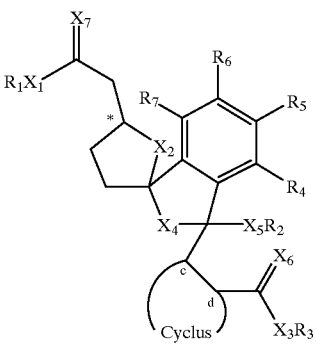

XXIV wherein:
$R_1$ to $R_7$, $X_1$ to $X_7$ and Cyclus are as defined in claim 1, or a pharmaceutically acceptable salt, ester, or ether, or other chemical equivalent, in any stereoisomeric and tautomeric form, or a mixture thereof in any ratio.

15. A process for preparing a compound of formula XVIII, XXII or XXIV, as claimed in any one of claim 3, 12, or 14, respectively, wherein —$X_3R_3$ is —$NH_2$, comprising reacting a compound of formula XVIII, XXII, or XXIV, wherein $X_3R_3$ is OH, with an amide source, and isolating a compound of formula XVIII, XXII or XXIV as claimed in any one of claim 3, 12, or 14.

16. The process according to claim 15, wherein the compound of formula XVIII is mumbaistatin.

17. A compound as defined in any one of claims 1–4, 6, 7 and 10–14, wherein at least one of $X_1$ to $X_7$ is O.

18. A compound of formula XVIII

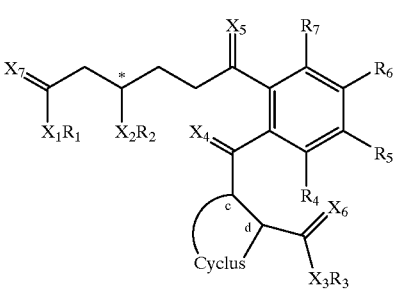

XVIII wherein:
$R_1$ and $R_3$ are independently selected from a cation, H, alkyl, and aryl;
$R_2$ is H, alkyl, aryl, or acyl;
$R_4$, $R_5$, $R_6$, and $R_7$ are independently selected from H, OH, halogen, alkyl, aryl, acyl, X-alkyl, and X-aryl, wherein X is O, NH, N-alkyl, or S, and wherein alkyl, acyl, and aryl are optionally substituted;
$X_1$, $X_2$, $X_3$, $X_4$, $X_5$, $X_6$, and $X_7$ are independently selected from O, NH, N-alkyl, and S; and
Cyclus is, together with the C atoms marked c and d, an optionally substituted saturated, partly unsaturated, or aromatic, carbocyclic or heterocyclic, simple or condensed ring system;
wherein the carbon marked with an asterisk has S configuration;

or a pharmaceutically acceptable salt, ester, or ether, or other chemical equivalent in any stereoisomeric or tautomeric form, or a mixture thereof in any ratio.

19. A compound as claimed in claim 18 wherein $R_1$, $R_2$, and $R_3$ are alkyl.

20. A process for preparing a compound of formula XVIII as claimed in claim 18, comprising reacting a compound of formula XVIII wherein at least one of $R_1$, $R_2$ and $R_3$ is H with an alkylating agent, and isolating a compound of formula XVIII as claimed in claim 18.

21. A compound of formula XIX

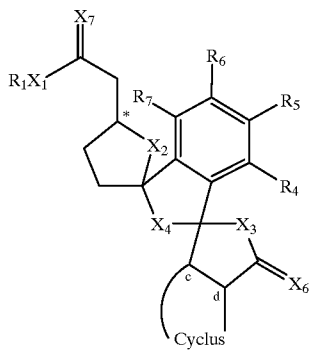

XIX wherein:

$R_1$ and $R_3$ are independently selected from a cation, H, alkyl, and aryl;

$R_2$ is H, alkyl, aryl, or acyl;

$R_4$, $R_5$, $R_6$, and $R_7$ are independently selected from H, OH, halogen, alkyl, aryl, acyl, X-alkyl, and X-aryl, wherein X is O, NH, N-alkyl, or S and wherein alkyl, acyl, and aryl are optionally substituted;

$X_1$, $X_2$, $X_3$, $X_4$, $X_5$, $X_6$, and $X_7$ are independently selected from O, NH, N-alkyl, and S, and Cyclus is, together with the C-atoms marked c and d, an optionally substituted saturated, partly unsaturated, or aromatic, carbocyclic or heterocyclic, simple or condensed ring system, wherein the carbon marked with an asterisk has S configuration;

or a pharmaceutically acceptable salt, ester, or ether, or other chemical equivalent, in any stereoisomeric or tautomeric form, or a mixture thereof in any ratio.

22. A compound as claimed in claim 21, wherein $R_1$ is alkyl, and $R_4$ is OH or alkoxy.

23. A process for preparing a compound as claimed in claim 21, comprising reacting a solution of the compound of formula XIX wherein $R_1$ is H and $R_4$ is OH with an alkylating agent, and isolating a compound of formula XIX as claimed in claim 21.

24. A process for preparing a compound as claimed in claim 22, comprising reacting a solution of the compound of formula XIX wherein $R_1$ is H and $R_4$ is OH in an alkyl alcohol with an acid, and isolating a compound of formula XIX as claimed in claim 22.

25. A compound of formula XX

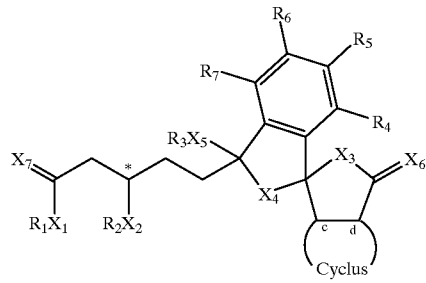

XX wherein:

$R_1$ and $R_3$ are independently selected from a cation, H, alkyl, and aryl;

$R_2$ is H, alkyl, aryl, or acyl;

$R_4$, $R_5$, $R_6$, and $R_7$ are independently selected from H, OH, halogen, alkyl, aryl, acyl, X-alkyl, and X-aryl, wherein X is O, NH, N-alkyl, or S and wherein alkyl, acyl, and aryl are optionally substituted;

$X_1$, $X_2$, $X_3$, $X_4$, $X_5$, $X_6$, and $X_7$ are independently selected from O, NH, N-alkyl, and S; and Cyclus is, together with the C atoms marked c and d, an optionally substituted saturated, partly unsaturated, or aromatic, carbocyclic or heterocyclic, simple or condensed ring system;

wherein the carbon marked with an asterisk has S configuration;

or a pharmaceutically acceptable salt, ester, or ether, or other chemical equivalent in any stereoisomeric or tautomeric form, or a mixture thereof in any ratio.

26. A compound of formula XXI

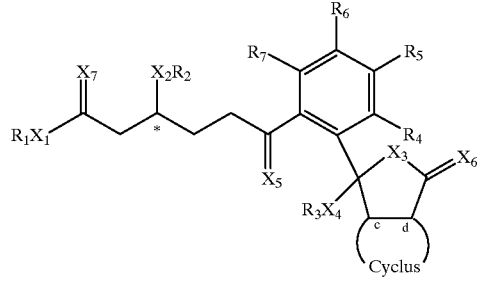

XXI wherein:

$R_1$ and $R_3$ are independently selected from a cation, H, alkyl, and aryl;

$R_2$ is H, alky, aryl, or acyl;

$R_4$, $R_5$, $R_6$, and $R_7$ are independently selected from H, OH, halogen, alkyl, aryl, acyl, X-alkyl, and X-aryl, wherein X is O, NH, N-alkyl, or S, and wherein alkyl, acyl, and aryl are optionally substituted;

$X_1$, $X_2$, $X_3$, $X_4$, $X_5$, $X_6$, and $X_7$ are independently selected from O, NH, N-alkyl, and S; and Cyclus is, together with the C-atoms marked c and d, an optionally substituted saturated, partly unsaturated, or aromatic, carbocyclic or heterocyclic, simple or condensed ring system;

wherein the carbon marked with an asterisk has S configuration;
or a pharmaceutically acceptable salt, ester, or ether, or other chemical equivalent in any stereoisomeric or tautomeric form, or a mixture thereof in any ratio.

27. A compound of formula XXII

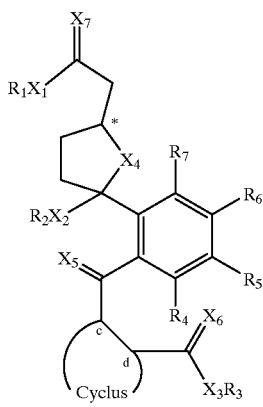

XXII wherein:
R$_1$ and R$_3$ are independently selected from a cation, H, alkyl, and aryl;
R$_2$ is H, alkyl, aryl, or acyl;
R$_4$, R$_5$, R$_6$, and R$_7$ are independently selected from H, OH, halogen, alkyl, aryl, acyl, X-alkyl, and X-aryl, wherein X is O, NH, N-alkyl, or S, and wherein alkyl, acyl, and aryl are optionally substituted;
X$_1$, X$_2$, X$_3$, X$_4$, X$_5$, X$_6$, and X$_7$ are independently selected from O, NH, N-alkyl, and S; and
Cyclus is, together with the C atoms marked c and d, an optionally substituted saturated, partly unsaturated, or aromatic, carbocyclic or heterocyclic, simple or condensed ring system;
wherein the carbon marked with an asterisk has S configuration;
or a pharmaceutically acceptable salt, ester, or ether, or other chemical equivalent, in any stereoisomeric and tautomeric form, or a mixture thereof in any ratio.

28. A compound of formula XXII as claimed in claim 27, wherein R$_1$ to R$_7$ are H, X$_3$ is NH, and R$_4$ is OH.

29. A compound of formula XXIV

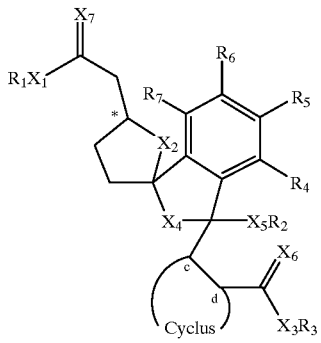

XXIV wherein:
R$_1$ and R$_3$ are independently selected from a cation, H, alkyl, and aryl;
R$_2$ is H, alkyl, aryl, or acyl;
R$_4$, R$_5$, R$_6$, and R$_7$ are independently selected from H, OH, halogen, alkyl, aryl, acyl, X-alkyl, and X-aryl, wherein X is O, NH, N-alkyl, or S, and wherein alkyl, acyl, and aryl are optionally substituted;
X$_1$, X$_2$, X$_3$, X$_4$, X$_5$, X$_6$, and X$_7$ are independently selected from O, NH, N-alkyl, and S; and
Cyclus is, together with the C atoms marked c and d, an optionally substituted saturated, partly unsaturated, or aromatic, carbocyclic or heterocyclic, simple or condensed ring system;
wherein the carbon marked with an asterisk has S configuration;
or a pharmaceutically acceptable salt, ester, or ether, or other chemical equivalent in any stereoisomeric and tautomeric form or mixtures thereof in any ratio.

30. A compound as claimed in any one of claims 1 to 4, 6, 7, 10 to 14, 17 to 21, and 23, wherein Cyclus is selected from phenyl, benzyl, naphthyl, phenanthrene, and anthraquinone.

31. A compound as claimed in claim 30, wherein Cyclus is unsubstituted, or substituted by at least one radical independently selected from OH, C$_1$–C$_4$-alkyl, —OC$_1$–C$_3$-alkyl, amino, nitro, halogen, —NH—C$_1$–C$_4$-alkyl, carboxy, and cyano.

32. A compound as defined in claim 30, wherein Cyclus is 3,8-dihydroxyanthraquinone.

33. A pharmaceutical composition, comprising an effective amount of a compound as claimed in any one of claims 1 to 4, 6, 7, 10 to 14, 17 to 19, 21, 22, and 25 to 32, and a pharmaceutically acceptable carrier.

34. A method of inhibiting glucose-6-phosphate translocase, comprising adding an inhibitory amount of a compound as claimed in any one of claims 1 to 4, 6, 7, 10 to 14, 17 to 19, 21, 22, and 25 to 32, to a glucose-6-phosphate.

35. A method of treating diabetes mellitus, comprising administering an effective amount of a compound as claimed in any one of claims 1 to 4, 6, 7, 10 to 14, 17 to 19, 21, 22, and 25 to 32, to a patient in need thereof.

36. A process for preparing a compound as claimed in any one of claims 1 to 4, 6, 7, 10 to 14, 17 to 19, 21, 22, and 25 to 32, comprising:

cultivating the microorganism *Streptomyces litmocidini*, DSM 11641, under aerobic conditions in a nutrient medium containing sources of carbon and nitrogen until mumbaistatin is produced in the culture filtrate;

subjecting the culture filtrate to ion-exchange chromatography at a pH of 5 to 8 to obtain isolated mumbaistatin; and converting the isolated mumbaistatin into said compound.

* * * * *

UNITED STATES PATENT AND TRADEMARK OFFICE
CERTIFICATE OF CORRECTION

PATENT NO. : 6,380,257 B1
DATED : April 30, 2002
INVENTOR(S) : Vértesy et al.

It is certified that error appears in the above-identified patent and that said Letters Patent is hereby corrected as shown below:

Column 23,
Line 6, "claim I" should read -- claim 1 --.

Column 24,
Line 51, "$X_7$ CyClus, C" should read -- $X_7$ Cyclus, c --.

Column 26,
Lines 26 and 31, "claim" should read -- claims --.

Signed and Sealed this

Twenty-fifth Day of June, 2002

Attest:

JAMES E. ROGAN
Attesting Officer
Director of the United States Patent and Trademark Office